United States Patent [19]
Tench et al.

[11] Patent Number: 5,262,022
[45] Date of Patent: Nov. 16, 1993

[54] METHOD OF ASSESSING SOLDERABILITY

[75] Inventors: D. Morgan Tench, Ventura; Dennis P. Anderson, Newbury Park, both of Calif.

[73] Assignee: Rockwell International Corporation, Seal Beach, Calif.

[21] Appl. No.: 706,142

[22] Filed: May 28, 1991

[51] Int. Cl.$^5$ .................................... G01N 27/26
[52] U.S. Cl. .................. 204/153.1; 204/400; 204/412; 204/434; 228/101; 228/103; 228/104
[58] Field of Search ............. 204/153.1, 153.11, 400, 204/404, 412, 434

[56] References Cited

U.S. PATENT DOCUMENTS

| | | | |
|---|---|---|---|
| 3,421,989 | 1/1969 | Haagen-Smit | 204/413 |
| 3,684,679 | 8/1972 | Smith et al. | 204/404 |
| 3,943,043 | 3/1976 | Billington et al. | 204/434 |
| 4,132,605 | 1/1979 | Tench et al. | 204/434 |
| 4,427,496 | 1/1984 | Katz | 204/153.1 |
| 4,654,126 | 3/1987 | Amelio et al. | 204/434 |
| 4,718,990 | 1/1988 | Hashimoto et al. | 204/434 |
| 4,725,339 | 2/1988 | Bindra et al. | 204/434 |

OTHER PUBLICATIONS

Kolthoff et al., *Polarography*, 2d. ed., vol. 1, (1952), p. 395

Primary Examiner—T. Tung
Attorney, Agent, or Firm—John C. McFarren

[57] ABSTRACT

A sequential electrochemical reduction method and apparatus for assessing solderability of electronic component leads and printed wiring boards. The method detects and quantifies the oxides present on copper, solder, and intermetallics that are detrimental to solderability. A solderable portion of the component to be tested is immersed in an electrolyte to form an electrode. An inert counter electrode and a reference electrode are also placed in the electrolyte. A current is passed from the inert counter electrode to the tested component, and the potential between the component and the reference electrode is recorded as a function of time. In a plot of the electrode potential versus the total charge passed, a series of inflection points identify and quantify particular metallic oxides present on the solder. The plot is compared with previous analyses of aged specimens having known oxide compositions that correlate with degradation of solderability. The method is useful for testing off-the-shelf components and for control of circuit board manufacturing and assembly processes.

8 Claims, 2 Drawing Sheets

| STEAM AGING (hours) | LOWER Sn OXIDE (mC/cm²) | HIGHER Sn OXIDE (mC/cm²) | WETTING TIME (seconds) |
|---|---|---|---|
| 0 | 2.1 | 0 | 2.0 |
| 0 | 1.9 | 0 | 2.9 |
| 0 | 1.5 | 0 | 2.0 |
| 0 | 1.6 | 0 | 2.3 |
| 0 | 1.1 | 0 | 2.9 |
| 0 | 1.4 | 0 | |
| 0 | Avg. 1.6 | 0 | Avg. 2.4 |
| 24 | 0 | 3.9 | 17.9 |
| 24 | 0 | 6.0 | 8.5 |
| 24 | 0 | 3.4 | 13.7 |
| 24 | 0 | 2.7 | 7.8 |
| 24 | 0 | 14.0 | 15.9 |
| 24 | 0 | | 14.3 |
| 24 | 0 | Avg. 6.0 | Avg. 13.0 |

METHOD OF ASSESSING SOLDERABILITY

TECHNICAL FIELD

The present invention relates to methods of testing electronic components and, in particular, to a method and apparatus for assessing the solderability of electronic component leads and printed wiring boards.

BACKGROUND OF THE INVENTION

A major cost problem experienced by the electronics industry is the loss of solderability of electronic components and printed circuit boards, particularly during storage. Poor solderability of component leads and printed wiring boards is believed to account for as much as 75% of solder joint failures. Because humid environments are known to exacerbate the problem, an electrochemical mechanism is clearly the cause of solderability degradation. In the lead-tin-copper solder system, for example, previous studies have determined that oxidation of the tin-lead (Sn-Pb) surface and underlying copper-tin (Cu-Sn) intermetallic layers is involved in the degradation process. In the past, however, the nature of the various oxides and their roles in the degradation of solderability remained obscure.

Traditional techniques typically employed in the prior art for surface analysis of circuit boards provide only subjective indicators of solderability. Currently used production test methods are also destructive by nature. Because degradation of solderability is known to involve an electrochemical mechanism, it is believed that solderability can be assessed more accurately and efficiently using electrochemical methods that provide in situ quantitative analysis of metallic oxides known to degrade solderability. In particular, there is a need for quantitative, nondestructive, electrochemical methods of solderability analysis that are easily applied for testing off-the-shelf components and for process control in the production environment.

SUMMARY OF THE INVENTION

The present invention comprises a sequential electrochemical reduction method and apparatus for assessing solderability of electronic component leads and printed wiring boards. The process is applicable to the lead-tin-copper solder system, as well as to solder systems comprising other metals and alloys. The method detects and quantifies metallic oxides known to degrade solderability when present on the solder surface and any intermetallic layers. The invention comprises a nondestructive method that provides a quantitative measure of the solderability of electronic components and printed wiring boards.

The electrochemical reduction method of the present invention is performed by placing the solderable portion of the component or circuit board to be tested in an electrolyte, such as a borate buffer solution. The immersed component forms a first electrode. A second, inert electrode and a third, reference electrode, such as a saturated calomel electrode, are also placed in the electrolyte. A small cathodic current is passed from the inert electrode to the tested component, and the potential between the component and the reference electrode is recorded as a function of time. In systems where the second, inert electrode has a stable voltage at the low currents used, it can also function as the reference electrode, thereby eliminating the need for a separate reference electrode. In a plot of the electrode potential versus the total charge passed (current multiplied by time), a series of inflection points or plateaux are observed in which the voltage level identifies a particular oxide or oxide mixture, and the associated charge is a measure of the thickness of that particular oxide.

The results achieved from the sequential electrochemical reduction performed on the tested component are compared to similar analytical results from baseline experiments on specimens exposed to various aging treatments. As determined by a wetting balance method, solderability of aged specimens has been found to correlate with results of the sequential electrochemical reduction method of analysis. Therefore, the analytical results from the tested component can be compared with baseline results obtained from aged specimens having known oxide and solderability characteristics to determine the solderability of the tested component.

A principal object of the invention is to improve solderability of electronic components and circuit boards by identifying and minimizing the types and amounts of metallic oxides that are present on the solder surfaces and intermetallic layers. A feature of the invention is the use of a sequential electrochemical reduction method to identify the metallic oxides that cause loss of solderability in electronic components. An advantage of the invention is that it provides a nondestructive method that is easy to perform and that yields a quantitative measure of the solderability of electronic components. This information is useful for controlling production soldering processes and for improving the manufacturing processes for printed wiring boards and other electronic components.

BRIEF DESCRIPTION OF THE DRAWINGS

For a more complete understanding of the present invention and for further advantages thereof, the following Detailed Description of the Preferred Embodiments makes reference to the accompanying Drawings, in which.

DETAILED DESCRIPTION OF THE PREFERRED EMBODIMENTS

Figures 1, 2:
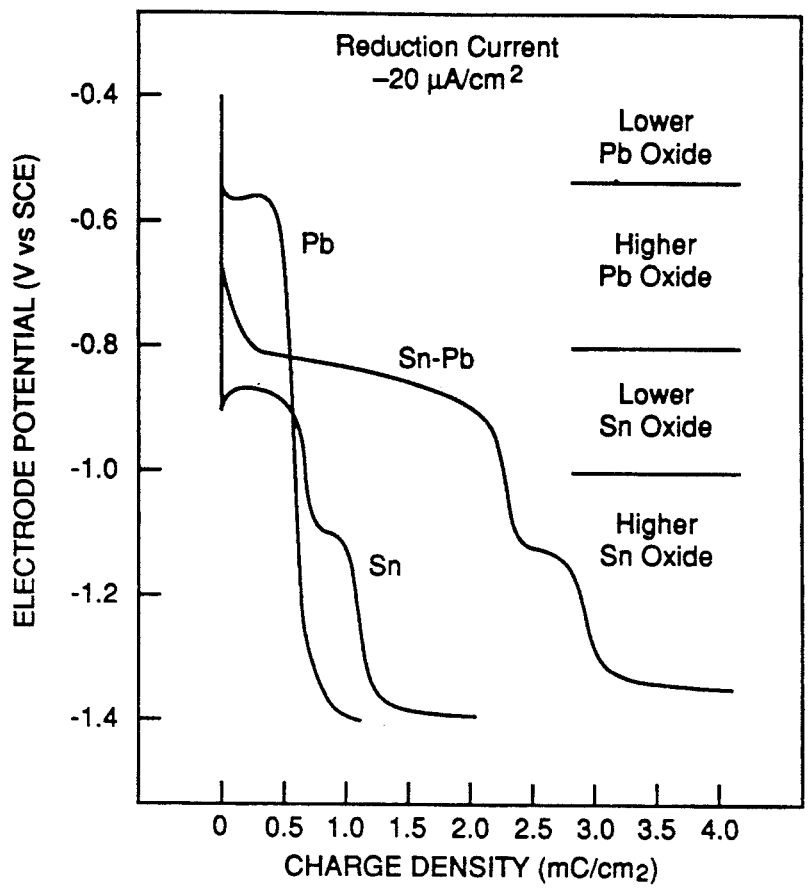
FIG. 1 is a graph of electrode potential versus charge density illustrating the sequential electrochemical reduction of the oxides of Sn, Pb, and eutectic Sn-Pb, and indicating the voltage ranges over which the various oxides are reduced.
FIG. 2 is a table showing a correlation between the presence of higher Sn oxides and poor solderability, as indicated by the long wetting times measured using a wetting balance method.

Solder coatings are widely used to protect copper in printed wiring boards and electronic component leads from oxidation that can lead to loss of solderability. A typical solder coating comprises eutectic Sn-Pb, for example, that can be applied directly by hot dipping or can be electroplated and then densified by reflowing (melting). Solderability of a finished component is affected by the metal ratios of the deposited solder, the thickness of the coating, the type of solder bath, the plating conditions, the presence of organic contaminants from plating bath additives, and the generation of breakdown products. When sufficiently thick and properly applied, such coatings can retain their original solderability even after several years of normal storage. However, Sn-Pb coatings frequently oxidize and lose solderability as a result of poor coating quality and/or a poor storage environment.

BASELINE EXPERIMENTS

A typical test specimen was a 1.5 mm diameter hard Cu wire, 2.5 cm in length, which was masked with Teflon® heat-shrink tubing to expose a 1 cm long section with a rounded end. The exposed section was plated with 10 μm of Cu from a standard non-additive pyrophosphate bath a 55° C., then with 12 μm of eutectic Sn-Pb from a standard fluoroborate bath at room temperature. During plating the wire cathode was rotated at 2000 rpm to control mass transport in the solution. A 60/40 Sn-Pb ratio was verified by atomic absorption analysis of specimens dissolved in acid solution and by X-ray fluorescence analysis. The Sn-Pb coating was reflowed in water soluble oil at 235° C. for minimal time prior to use. Specimens were subjected to various steam aging and anodization treatments to produce oxidized samples.

Electrochemical reduction was performed on the specimens in a borate buffer solution (9.55 g/L sodium borate and 6.18 g/L boric acid) at a pH of 8.4 under an argon atmosphere in a 200 mL glass cell having separate compartments for a Pt counter electrode and a reference saturated calomel electrode (SCE). Other electrolytes compatible with the Cu-Sn-Pb system may be used in conjunction with alternative types of reference electrodes and counter electrodes of other inert materials. All electrochemical experiments were performed using a potentiostatgalvanostat (PAR model 173, EG&G Princeton Applied Research Corp., Princeton, N.J.). Solderability tests were performed using a modified Wilhelmy wetting balance in conjunction with a digital oscilloscope (Nicolet model 2090, Nicolet Instrument Corp., Madison, Wis.).

A constant reduction current of $-20$ $\mu A/cm^2$ was applied to the specimen electrode in the borate buffer solution and the electrode potential versus the reference SCE electrode was recorded as a function of time. Inflection points, which are believed to correspond to the reduction of PbO, SnO, and $SnO_2$, were observed at approximately $-0.6$ V, $-0.9$ V, and $-1.1$ V, respectively. From cyclic voltammetric measurements involving pure Pb and Sn electrodes, it was determined that there was a one-to-one correspondence between the anodic charge passed during formation of the oxides by anodization and the cathodic charge required for their reduction. This result indicates that the electrochemical reduction method of the present method provides a quantitative measure of the amount of each surface oxide present. In addition, the fact that such thick oxides can be sequentially reduced indicates appreciable oxide porosity. Heavily oxidized specimens were consistently found to exhibit very poor solder wetting characteristics, thereby establishing a link between the presence of higher Sn oxides and the loss of solderability.

FIG. 1 illustrates representative curves obtained from sequential electrochemical reduction analysis of the oxides formed on Sn, Pb, and eutectic Sn-Pb under mildly oxidizing conditions. These curves plot electrode potential versus charge density (which equals current density ×time). The curves comprise a series of inflection points or plateaux in which the voltage level identifies a particular oxide, and the associated charge is a measure of the oxide thickness. In Sn-Pb coatings, the two Pb oxides normally are present only in small concentrations. It is convenient to refer to the Sn oxides as the lower oxide (believed to be predominantly SnO), which reduces at a voltage of approximately $-0.8$ V to $-1.0$ V, and the higher oxide (believed to be predominantly $SnO_2$), which reduces at a voltage of approximately $-1.0$ V to $-1.4$ V (versus the reference SCE electrode). Negative voltage peaks are believed to indicate a duplex structure having an outer layer that is more difficult to reduce than the underlying material.

FIG. 2 is a table of data obtained from testing Sn-Pb solder specimens as-reflowed (zero aging) and after steam aging (24 hours). The charge density for reduction (measured in $mC/cm^2$) is an indication of the amount and type of oxides present. The wetting time is a measure of the time in seconds to obtain two-thirds of the maximum theoretical wetting force obtainable by a wetting balance method. The charge density data and the wetting time data are reported for similarly prepared specimens, but not the identical specimens. It should also be noted that because of the high thermal inertia of the relatively thick test specimens used in this study, wetting times are generally higher than would be expected for thinner specimens, but it is the relative values that are important. From the data in FIG. 2 it can be seen that the presence of large amounts of higher Sn oxide detected by the electrochemical reduction method of the present invention correlates with a loss in solderability, as indicated by the long wetting times. The present method has also been useful in detecting more subtle losses in solderability than those presented FIG. 2.

The copper oxides, $Cu_2O$ and $CuO$, and the Cu-Sn intermetallic oxides can also be detected readily by the sequential electrochemical reduction method of the present invention. The principal Cu-Sn intermetallic oxide was investigated by plating standard Cu-plated wire specimens with 3 μm of Sn and heating under a vacuum at 200° C. for three days to convert all of the Sn to $Cu_3Sn$. These specimens were found to be almost completely unwettable by solder. A layer of native oxide, about 5 atom layers thick, was found to be completely reduced in the argon-saturated borate buffer electrolyte. The reduced surface was stable in the de-aerated solution, but exposure of the reduced surface to air for only 5 seconds resulted in regrowth of 5 atom layers of oxide that exhibited a well-defined plateau at about the same voltage as observed for SnO reduction ($-0.9$ V). Overnight, this oxide thickened to greater than 10 atom layers, and the reduction curve exhibited a long tail, indicating the presence of the more stable Sn oxide. These results show that a major problem with the $Cu_3Sn$ intermetallic is the fast rate at which relatively thick oxide layers form on its surface. It is believed that this is a consequence of local cell action in which Cu acts as the cathode.

ASSESSING SOLDERABILITY

The method of assessing solderability of an electronic component is essentially the same as described above in the baseline experiments. An electronic component lead to be tested is immersed in an electrolyte to form a first electrode. A second, inert counter electrode and a third, reference electrode are also placed in the electrolyte. A negative current is passed between the component and the second electrode while the potential between the component and the reference electrode is recorded as a function of time. As described above, in systems where the second, inert electrode has a stable voltage at the low currents used, it can also function as the reference electrode, thereby eliminating the need for a separate reference electrode. The voltage versus charge density curve obtained indicates the various types and amounts of oxides on the component lead. This data is compared with known results from the baseline experiments to characterize the solderability of the component lead.

Figure 3:
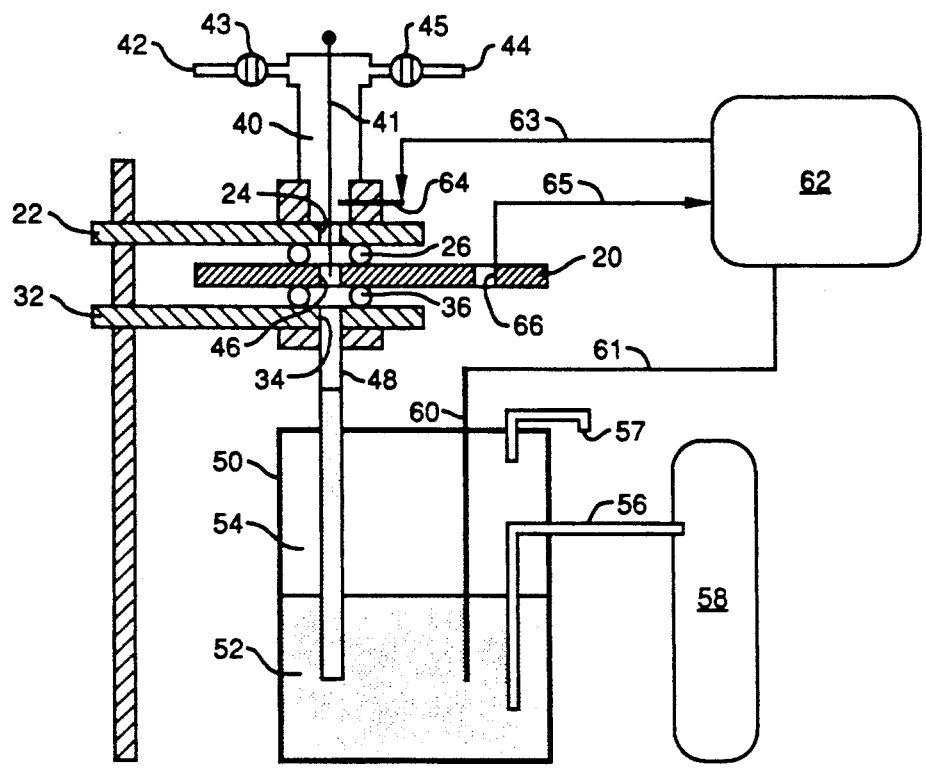
FIG. 3 is a schematic diagram of an apparatus for assessing the solderability of a printed wiring board through-hole electrode.
Figure 4:
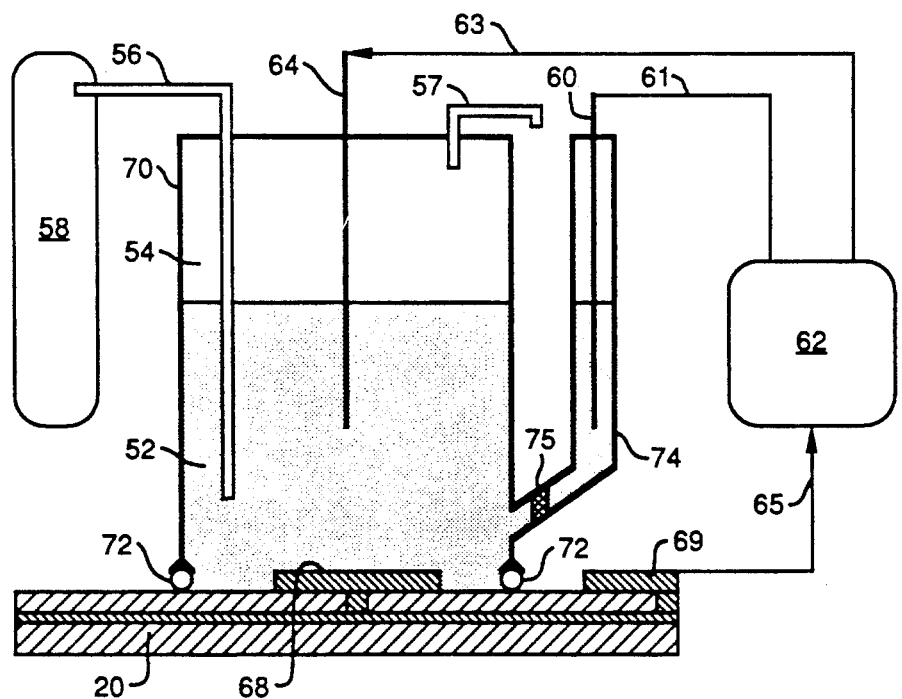
FIG. 4 is a schematic diagram of an apparatus for assessing the solderability of a printed wiring board surface-mount pad electrode.

Assessing solderability of printed wiring boards can be accomplished with apparatus similar to those depicted schematically in FIGS. 3 and 4. The apparatus of FIG. 3 is suitable for testing through-hole solder points and the apparatus of FIG. 4 is suitable for testing solder pads used for surface-mount components. The same reference numerals are used in FIGS. 3 and 4 to identify the same or similar elements of the two devices. In FIG. 3, a wiring board 20 having bare or solder-coated printed copper circuitry to be tested for solderability is clamped between an upper jaw 22 and a lower jaw 32. Upper jaw 22 has an aperture 24 and an O-ring 26. O-ring 26 is attached to the lower side of jaw 22 and encircles aperture 24. Lower jaw 32 has an aperture 34 and an O-ring 36. O-ring 36 is attached to the upper side of jaw 32 and encircles aperture 34. A chamber 40 having a centering pin 41 is mounted atop jaw 22. Chamber 40 is mounted on jaw 22 so that pin 41 can extend downward through aperture 24 in jaw 22. Pin 41 may be used to position a through-hole electrode 46 of printed wiring board 20 between O-rings 26 and 36. When circuit board 20 is positioned by pin 41 and clamped between jaws 22 and 32, O-rings 26 and 36 provide a seal around through-hole electrode 46 in preparation for assessing solderability of the bare or solder-coated printed copper circuitry associated with through-hole 46.

A tube 48 of inert material extends from aperture 34 of lower jaw 32 into a sealed electrolyte reservoir 50. Reservoir 50 contains an electrolyte solution 52 and an inert gas 54, such as argon, above electrolyte 52. Electrolyte 52 may comprise any electrolyte compatible with the particular solder system, such as a borate buffer solution (9.55 g/L sodium borate and 6.18 g/L boric acid at a pH of 8.4, for example) suitable for use with the Cu-Sn-Pb system. A wide variety of electrolytes (e.g., borates, citrates, sulfates, nitrates, etc.) will provide acceptable results. However, electrolytes having a neutral or alkaline pH, and from which strong metal complexing agents (e.g., chloride, bromide, etc.) have been excluded, will yield the most accurate measurements. Inert gas 54 is supplied to reservoir 50 through a gas line 56 from a gas source 58. Gas 54 can exit reservoir 50 through a gas outlet valve 57. Inert gas 54, such as argon, is used to flush air from the system to eliminate erroneous electrochemical reduction data caused by the presence of oxygen. A reference electrode 60, which may comprise a saturated calomel electrode (SCE), for example, extends into reservoir 50 and into electrolyte 52. Reference electrode 60 may be placed in a separate compartment within reservoir 50 to minimize the effects of any contamination of the electrolyte.

A control system 62, comprising a current source, a voltage meter, and a recording device, is connected by leads 61, 63, and 65, respectively, to reference electrode 60, an inert counter electrode 64 (such as platinum, for example) that extends within the chamber of chamber 40, and a through-hole contact 66 that is connected by the printed circuitry of circuit board 20 to through-hole electrode 46. In an alternative embodiment, if inert electrode 64 has a stable voltage at the low currents used, it can also function as the reference electrode, thereby eliminating the need for separate reference electrode 60.

Through-hole electrode 46 is tested for solderability by using pin 41 to position through-hole 46 of circuit board 20 between O-rings 26 and 36. Circuit board 20 is clamped securely by jaws 22 and 32 so that O-rings 26 and 36 form a seal around electrode 46. Pin 41 may then be withdrawn from through-hole 46. Chamber 40 is connected to a vacuum line 42 controlled by a valve 43 and to an inert gas line 44 controlled by a valve 45. Valve 45 is opened to flush chamber 40, through-hole 46, and tube 48 with inert gas to remove oxygen from the system. Thereafter, valve 45 is closed and valve 43 is opened so that electrolyte 52 is drawn up through tube 48, through and around electrode 46, and into chamber 40 above counter electrode 64.

With electrolyte 52 drawn into chamber 40, system 62 provides a constant current, in the range of about 10–1000 $\mu A/cm^2$, through line 63, electrode 64, electrolyte 52, electrode 46, through-hole 66, and line 65 back to source 62 (i.e., a negative current is supplied from through-hole electrode 46 of circuit board 20 to counter electrode 64). The current provided by source 62 causes sequential electrochemical reduction of the oxides on the bare or solder-coated copper circuitry of through-hole electrode 46. Current greater or less than the recommended 10–1000 $\mu A/cm^2$ may be used: a low current provides high resolution at the expense of time; a high current provides fast results but low resolution. While supplying current, system 62 measures and records the electrode potential between through-hole electrode 46 and reference electrode 60 as a function of time. The time factor can be converted to charge density by multiplying the current density by the elapsed time. As described above, the readout of electrode potential versus charge density (or time) produces a series of inflection points or plateau that indicate the particular oxides being reduced as well as the thicknesses of the various oxide layers. The results can be compared to the baseline data to determine the specific oxides present on electrode 46 and the associated measure of solderability. Although a typical circuit board 20 comprises a multiplicity of through-hole electrodes, a small number of through-holes (a statistical sample) can be tested to characterize the solderability of the entire circuit board 20.

The apparatus shown schematically in FIG. 4 is simply a modification of the foregoing system suitable for testing a solder pad electrode 68 on circuit board 20 instead of a through-hole. The modified apparatus comprises an open-bottom vessel 70 that has an O-ring 20 around its bottom rim. Vessel 70 is placed atop board 20 so that O-ring 72 surrounds solder pad electrode 68. Vessel 70 typically includes a lid or port (not shown) for adding electrolyte 52. A clip (not shown) can be used to secure board 20 to the bottom of vessel 70 so that a tight seal is maintained by O-ring 72 around solder pad electrode 68. Inert gas 54 is supplied to vessel 70 by line 56 from gas source 58. After a seal is made around pad electrode 68, vessel 70 may be flushed with inert gas 54, with air escaping from vent 57. Vessel 70 may include a connected chamber 74 with a porous glass frit 75 for partially isolating reference electrode 60. System 62 provides current for electrochemical reduction of the metallic oxides on solder pad electrode 68. Current is provided from control system 62 through line 63, electrode 64, electrolyte 52, pad electrode 68, circuit-connected pad electrode 69, and line 65 back to system 62. System 62 also measures and records the electrode potential between pad electrode 68 and reference electrode 60 as a function of time during electrochemical reduction of the metallic oxides on pad electrode 68. Electrode 60 may be placed in chamber 74, as illustrated, or electrode 64 may function as the reference electrode in some circumstances, thereby eliminating the need for a separate reference electrode 60. As described above, the record of electrode potential versus time can be compared to the baseline data to determine the specific oxides present on pad electrode 68 and the associated measure of solderability.

Although the present invention has been described with respect to specific embodiments thereof, various changes and modifications can be carried out by those skilled in the art without departing from the scope of the invention. Therefore, it is intended that the present invention encompass such changes and modifications as fall within the scope of the appended claims.

We claim:

1. A method of assessing solderability of an electronic component, comprising the steps of:
   placing a solderable portion of the component in contact with an electrolyte to form a first electrode;
   placing a second electrode in contact with said electrolyte;
   connecting said first and second electrodes to a source of electric power and passing a current between said first and second electrodes;
   reducing metallic oxides present on said solderable portion of the component;
   measuring voltage and current between said first and second electrodes as a function of time during said reduction of metallic oxides; and
   analyzing said voltage and current versus time measurements to determine solderability of the component.

2. The method of claim 1, wherein the step of analyzing further comprises:
   correlating said voltage and current versus time measurements with predetermined baseline data from test specimens having known solderability.

3. The method of claim 1, further comprising the steps of:
   providing a sealable reservoir for containing said electrolyte; and
   flushing said electrolyte with an inert gas to eliminate oxygen from said electrolyte.

4. A method of assessing solderability of an electronic component, comprising the steps of:
   placing a solderable portion of the component in contact with an electrolyte to form a first electrode;
   placing a second electrode in contact with said electrolyte;
   providing a third, reference electrode in contact with said electrolyte;
   connecting said first and second electrodes to a source of electric power and passing a current between said first and second electrodes;
   reducing metallic oxides present on said solderable portion of the component;
   measuring current between said first and second electrodes and voltage between said first and third electrodes as a function of time during said reduction of metallic oxides; and
   analyzing said voltage and current versus time measurements to determine solderability of the component.

5. A method of sequential electrochemical reduction of metallic oxides for assessing solderability of an electronic component, comprising the steps of:
   providing an electrolyte in a reservoir;
   placing a solder coated portion of the component in contact with said electrolyte to form a first electrode;
   placing a second, inert electrode in contact with said electrolyte;
   connecting said first and second electrodes to a source of electric power;
   sequentially reducing metallic oxides on said solder coated portion of the component by passing a current between said first and second electrodes;
   measuring voltage and current between said first and second electrodes as a function of time during said sequential reduction of metallic oxides; and
   analyzing said voltage and current versus time measurements to determine solderability of the component.

6. The method of claim 5, wherein the step of analyzing further comprises:
   correlating said voltage and current versus time measurements with predetermined baseline data from test specimens having known solderability.

7. A method of sequential electrochemical reduction of metallic oxides for assessing solderability of an electronic component, comprising the steps of:
   providing an electrolyte in a reservoir;
   placing a solder coated portion of the component in contact with said electrolyte to form a first electrode;
   placing a second, inert electrode in contact with said electrolyte;
   placing a third, reference electrode in contact with said electrolyte;
   connecting said first and second electrodes to a source of electric power;
   sequentially reducing metallic oxides on said solder coated portion of the component by passing a current between said first and second electrodes;
   measuring current between said first and second electrodes and voltage between said first and third electrodes as a function of time during said sequential reduction of metallic oxides; and
   analyzing said voltage and current versus time measurements to determine solderability of the component.

8. The method of claim 7, further comprising the steps of:
   eliminating oxygen from said electrolyte in said reservoir, said reservoir comprising a sealable reservoir; and
   placing a saturated calomel electrode as said third reference electrode in a compartment of said reservoir.

* * * * *